(12) United States Patent
Bishay

(10) Patent No.: US 6,293,962 B1
(45) Date of Patent: *Sep. 25, 2001

(54) METHOD FOR MAINTAINING ENVIRONMENTAL CONDITIONS FOR A MEDICAL DEVICE

(75) Inventor: Jon M. Bishay, Woodinville, WA (US)

(73) Assignee: Agilent Technologies, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 33 days.

(21) Appl. No.: 08/706,487

(22) Filed: Sep. 4, 1996

(51) Int. Cl.[7] ..................................................... A61N 1/02
(52) U.S. Cl. ............................................................ 607/1
(58) Field of Search ........................ 337/2, 1, 12; 62/3.3, 62/3.6, 3.62, 3.7; 429/120; 607/1, 2

(56) References Cited

U.S. PATENT DOCUMENTS

| | | |
|---|---|---|
| 4,840,855 | 6/1989 | Foti et al. .............................. 429/120 |
| 5,054,545 | 10/1991 | Ghaemian ........................ 165/104.33 |
| 5,132,874 | 7/1992 | Chandler et al. ..................... 361/722 |
| 5,160,357 | 11/1992 | Faber .................................. 55/385.2 |
| 5,215,834 | 6/1993 | Reher et al. ........................... 429/62 |
| 5,229,702 | 7/1993 | Boehling et al. ........................ 320/2 |
| 5,449,571 | 9/1995 | Longardner et al. ................ 429/120 |
| 5,464,428 | * 11/1995 | Hill . |
| 5,483,799 | * 1/1996 | Dalto ...................................... 62/3.7 |
| 5,516,600 | 5/1996 | Cherng .................................. 429/62 |
| 5,603,220 | * 2/1997 | Seaman .................................. 62/3.7 |

\* cited by examiner

*Primary Examiner*—William E. Kamm

(57) ABSTRACT

This invention relates to a method for maintaining an electrotherapy device wherein the air temperature of the electrotherapy device environment is monitored and then adjusted based on the results of the monitoring step. The method may be accomplished by using an environmental carrying case. Additionally it is contemplated that air of the environment may be circulated to produce an ambient temperature. Monitoring the temperature may accomplished by using a thermostat or a temperature sensitive switch. In a preferred embodiment, a cooling means is activated when the temperature reaches a threshold temperature between 25° C. and 50° C., more preferably 43° C. The cooling means may be a fan. In a preferred embodiment, a heating means is activated when the temperature reaches a threshold temperature between –10° C. and 20° C., more preferably 0° C. The heating means may be heat strips.

11 Claims, 2 Drawing Sheets

METHOD FOR MAINTAINING ENVIRONMENTAL CONDITIONS FOR A MEDICAL DEVICE

BACKGROUND OF THE INVENTION

1. Field of the Invention

This invention relates to methods for maintaining environmental conditions for an electrotherapy medical device in order to allow immediate use in an emergency situation and to improve the shelf life and reliability of the device. More specifically, this invention relates to maintaining the storage temperature for an automatic or semi-automatic external defibrillator (AED) within a specified temperature range.

2. Description of the Prior Art

Over the last several years medical devices have become more portable and have begun moving into the hands of first responders. As a result, equipment that was once available only in a hospital, having a temperature controlled environment, is now being transported and stored in environments that are not predictable or controlled. AEDs are frequently stored in emergency vehicles and are transported by firefighters, police officers and ambulances directly to the scene of a sudden cardiac arrest. Although the size and portability of AEDs have made them more readily transportable and increased their availability in the field, they are still manufactured from many temperature sensitive components.

For example, an important component of an AED is the power source. Typically, portable AEDs rely on a battery pack to provide power to the unit. Fluctuations in storage temperature of the device can compromise the performance, reliability and life of the battery. Both alkaline and lithium batteries are affected by variations in storage temperature. Although lithium batteries typically have a longer shelf life than alkaline batteries, they are more susceptible to fluctuations in storage temperature. As a result a device that operates using a lithium or alkaline battery may have reduced reliability if the storage temperature is not maintained within a desired range. Additionally, as the temperature of the battery decreases the capacity of the battery decreases. Low battery capacity lowers the number of shocks that a defibrillator can deliver with that battery.

Another temperature sensitive component of an AED are the hydrogel coated electrode pads. These pads are applied to the skin of the person thought to be in need of defibrillation. The pads allow the AED to receive electrocardiogram (ECG) information from the patient so that the AED can analyze the ECG and determine whether a shock is advisable. Once the AED determines that a shock is advisable, the hydrogel pads conduct the shock through the patient's skin and to the heart. In view of the high amount of water contained in the hydrogel layer of the pads it is important that the water content of the hydrogel is not changed as a result of the storage temperature. For example, when storage temperatures are above 55° C., the hydrogel layer begins to dry out, changing the conductive and cohesive characteristics of the gel. Alternatively, as the temperature is lowered below 10° C., the hydrogel could begin to freeze, again changing the conductive and cohesive characteristics of the gel.

Another temperature sensitive component of an AED is the liquid crystal display (LCD). When an LCD becomes too cold, the crystals begin to freeze and the response of the display is slowed considerably. For example, when the temperature reaches −20° C. to −10° C. (−4° F. to 14° F.) it can take several seconds for the screen to register the display command. Since every second in an emergency response situation is critical, a delay of even a few seconds in the screen response per prompt could cumulatively be very significant; particularly since the survival rate of patients receiving a shock from an AED substantially improves the sooner after the incident the shock is applied. When an LCD becomes too hot, the LCD is unable to selectively polarize the crystals and the display will appear dark because voltage across the LCD is applied to all crystals. Loss of the LCD could be critical especially for an AED that displays an ECG or where the AED is being used by a hearing impaired person who is relying on the LCD for prompting.

Digital electronic circuits and components are also temperature sensitive. It is well known that transistor offset and bias currents are affected by both high and low temperatures. For example, a circuit with a range of 2–20 pA could increase to 0.5 nA if the temperature exceeds the $T_{max}$ for that circuit. The effects of temperature on the offset and bias current for a given circuit are typically published in the specifications for that circuit.

The prior art has recognized the temperature sensitivity of certain electronic devices. For example, video equipment is sensitive to storage temperature. Video tapes may become damaged from exposure to either high or low temperatures. Additionally, the video camera itself may become damaged if used after storage at a low temperature. Cruisers, Inc. (Brighton, Mich.) manufactures a carrier for video equipment for use in police vehicles. This carrier is capable of warming or cooling the temperature around the video equipment, as necessary.

As discussed above, batteries are affected by storage temperature. As a result of a number of methods and devices have been developed for controlling the storage temperature of the battery. Several patents have issued directed to thermal management systems for lead acid batteries used in cars. For example, U.S. Pat. No. 5,449,571 (Longardner et al.) teaches using a phase change material (PCM) filled housing to control the temperature around the battery. The PCMs can absorb heat generated by batteries during operation and can assist in maintaining a higher battery temperature in cold conditions.

Another example of a temperature insulator for a battery is shown in U.S. Pat. No. 5,516,600 (Cherng). The Cherng patent teaches the use of barrier film with expandable chambers to provide insulation. Chambers are filled with a fluid and may be fabricated as a blanket or bellows.

An alternative system for cooling and heating batteries is shown in U.S. Pat. No. 5,215,834 (Reher et al.) and U.S. Pat. No. 4,840,855 (Foti et al.). Reher et al. heats or cools a battery depending upon the storage temperature and the state of the charge by using a reversible fan. Conduits access either heated or unheated air which is then pumped over the battery, depending upon the temperature needs. Foti et al. provide a housing having inner and outer layers fabricated from waterproof material with an insulative layer therebetween. An electric heater coil provides additional heat, as necessary.

U.S. Pat. No. 5,229,702 (Boehling et al.) is directed to a device for protecting rechargeable batteries in a lighting unit. Boehling et al. uses a thermoelectric pump to cool the battery enclosure and heat sinks to warm the enclosure. Boehling et al. also teach a device for maintaining the life of a vehicle battery by keeping the temperature within optimal ranges.

What is needed is a way to maintain the storage environment for electrotherapy devices so that the effects of heat and cold do not prevent the equipment from being ready for immediate use in an emergency or compromise the performance of the components when the device is in use. No apparatus or methods currently known meets the specialized storage needs of electrotherapy devices such as AEDs.

None of the devices or methods taught in the prior art address the need to maintain the environmental conditions for a medical device or take into consideration the sensitivity of various components of a device.

SUMMARY OF THE INVENTION

In a preferred embodiment, this invention relates to a method for maintaining an electrotherapy device wherein the air temperature of the electrotherapy device environment is monitored and then adjusted based on the results of the monitoring step. The method may be accomplished by using an environmental carrying case. Additionally, adjusting the air temperature may be accomplished by circulating the air in the electrotherapy device environment. Monitoring the temperature may be accomplished by using a thermostat one or more temperature sensitive switches. In a preferred embodiment, a cooler is activated when the temperature reaches a threshold temperature between 25° C. and 50° C., more preferably 43° C. (110° F.). The cooler may be a fan. In a preferred embodiment, a heater is activated when the temperature reaches a threshold temperature between −10° C. and 20° C., more preferably 0° C. (32° F.). The heater may be heat strips.

The invention is explained in more detail below with reference to the drawings.

DESCRIPTION OF THE PREFERRED EMBODIMENTS

This invention is directed to a method for maintaining the environmental temperature conditions for a battery operated device. A diagram showing an insulated case accomplishing this method is shown in FIG. 1.

Figure 1:
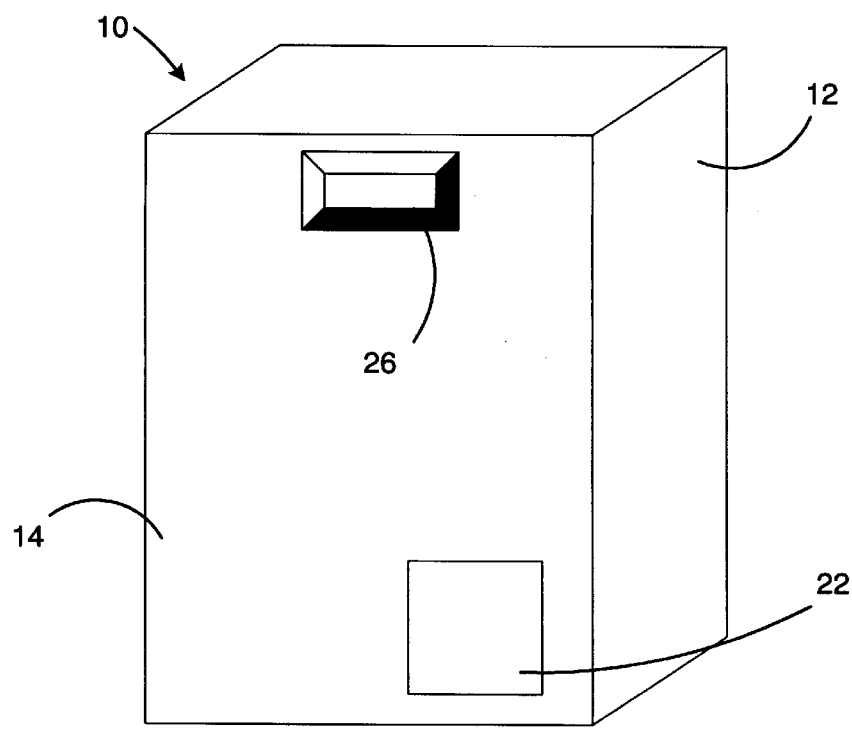
FIG. 1 is a frontal view of an environmental case, with the door closed.

As shown in FIG. 1, an environmental case 10 has a container portion 12, for holding the device and a door 14. Ideally, the case 10 is made of a rugged material, such as sheet metal. The dimensions of the case depend on the size of the AED to be housed. In one embodiment, the case 10 is dimensioned so that it will store a small AED. A small AED could have dimensions of approximately 25 cm×22 cm×12 cm. The internal dimensions of the case 10 should be sufficiently larger than the AED to allow air flow around the device in order to efficiently adjust environmental conditions within the case 10.

Figure 2:
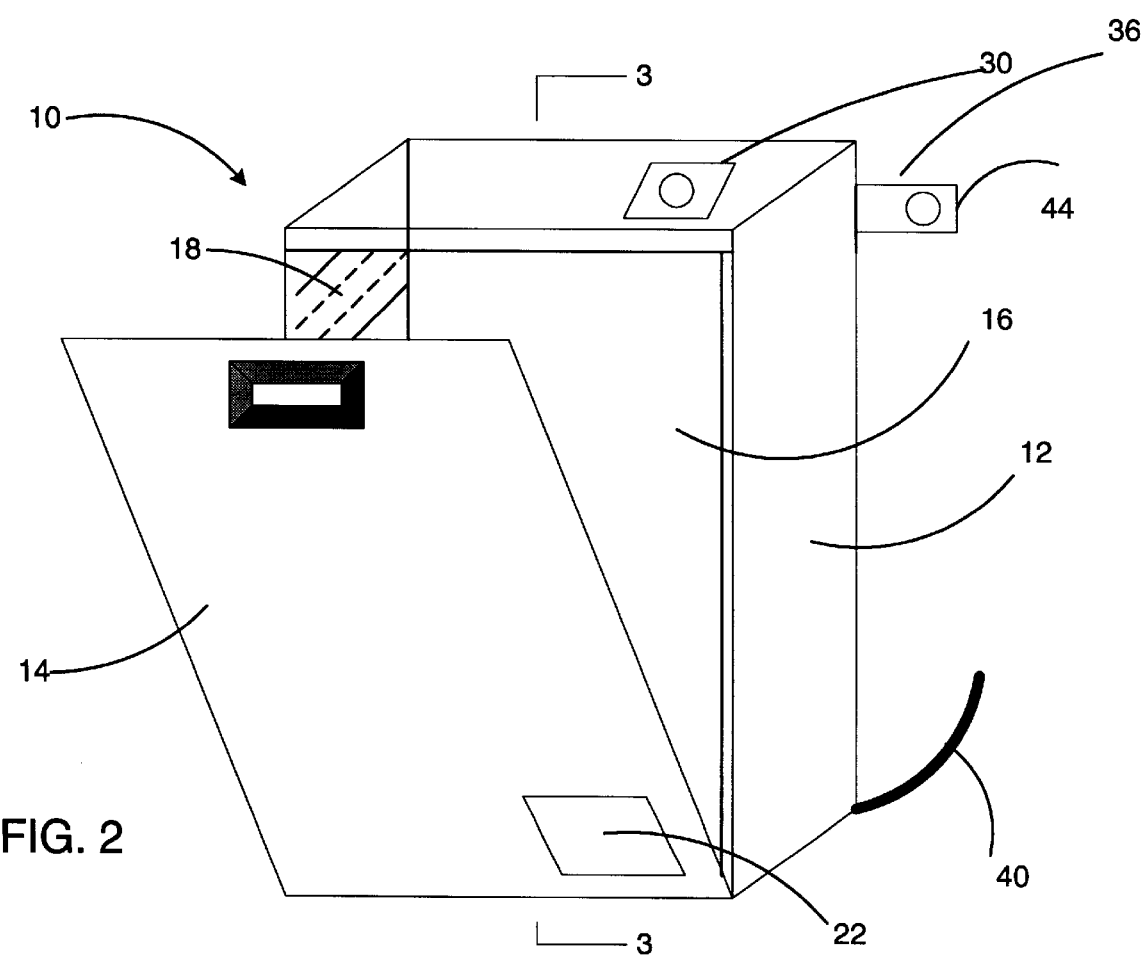
FIG. 2 is a perspective view of an environmental case, with the door open.

As more clearly shown in FIG. 2, the interior walls 16 of the case 10 may also be lined with insulative material 18 such as foam or other suitable material. A door 14 is attached to one end of the container portion 12 by, for example, a hinge 20. When the case 10 is manufactured from an opaque material, such as sheet metal, the door 14 may be fabricated so that a section of the door is comprised of a transparent panel 22. The transparent panel insert may be fabricated from any sturdy transparent material, such as safety glass or Plexiglas®.

The door 14 is held in the closed position on the case 10 by means of a latch mechanism 24. A suitable latch mechanism would have, for example, a male end 24A on the door and a corresponding receiving female end 24B on the case. The latch 24 would typically be located on the opposite end of the door 14 from the hinge 20. Other latching mechanisms suitable for keeping the door 14 of the case 10 closed would also be appropriate. A handle 26 is located on the exterior surface of the door 14.

Figure 3:
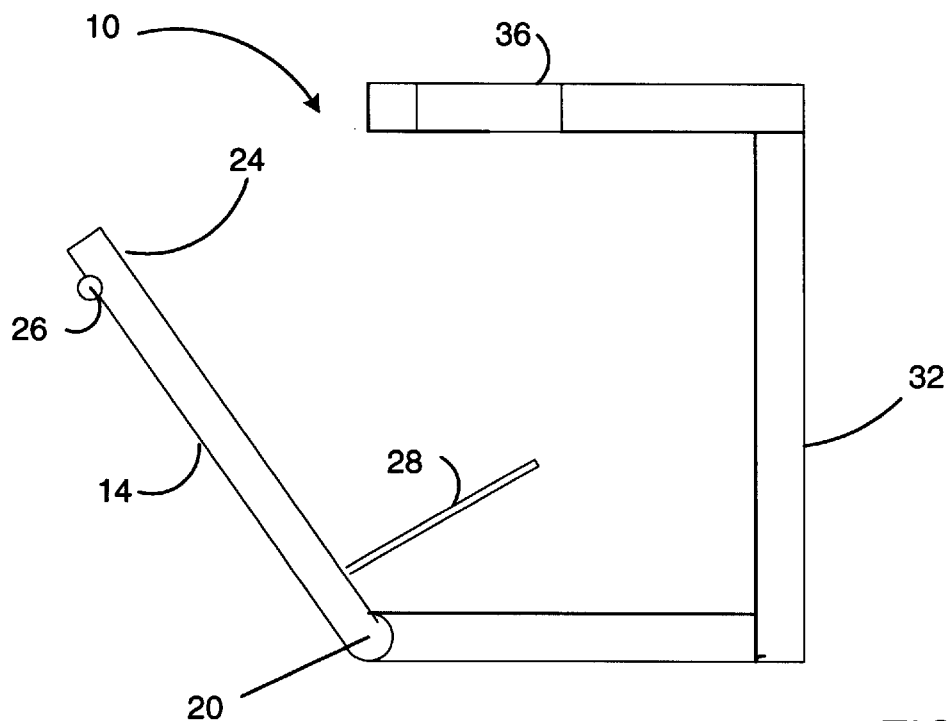
FIG. 3 is a cross-sectional side view of an environmental case, along the lines 3—3 shown in FIG. 2.

As shown in FIG. 3, the door 14 may be configured so that it has one or more ledges 28 on which the device sits. Ledge 28 provides the advantage that when the door 14 is opened, the ledge 28 rotates the device out of the container 12 so that the device handle is quickly and easily reachable during deployment. Additionally the ledge 28 may be configured so that, in the closed position, air flow is permitted underneath the device.

The case 10 contains a thermostat 34 to measure the temperature inside the case when the defibrillator is stored. The thermostat 34 is configured such that when the temperature within the case 10 reaches a temperature above a threshold amount a switch is activated and a signal is transmitted to a cooler, for example, a fan 36 configured within the case 10 to circulate cooler air from outside the case 10 and lower the temperature within the case 10. The threshold temperature is between 25° C. and 50° C., more preferably 43° C. Ideally, the fan 36 will be configured so that it will switch on and begin circulating air so that the temperature in the case does not reach or exceed the desired storage temperature range. The thermostat 34 may also be configured such that when the temperature within the case reaches a temperature below a threshold amount a switch is activated and a signal is transmitted to a heater, such as one or more silicon strips 40 which then begin to emit heat in order to increase the temperature within the case 10. The threshold temperature is between −10° C. and 20° C., more preferably 0° C.

Figure 4:
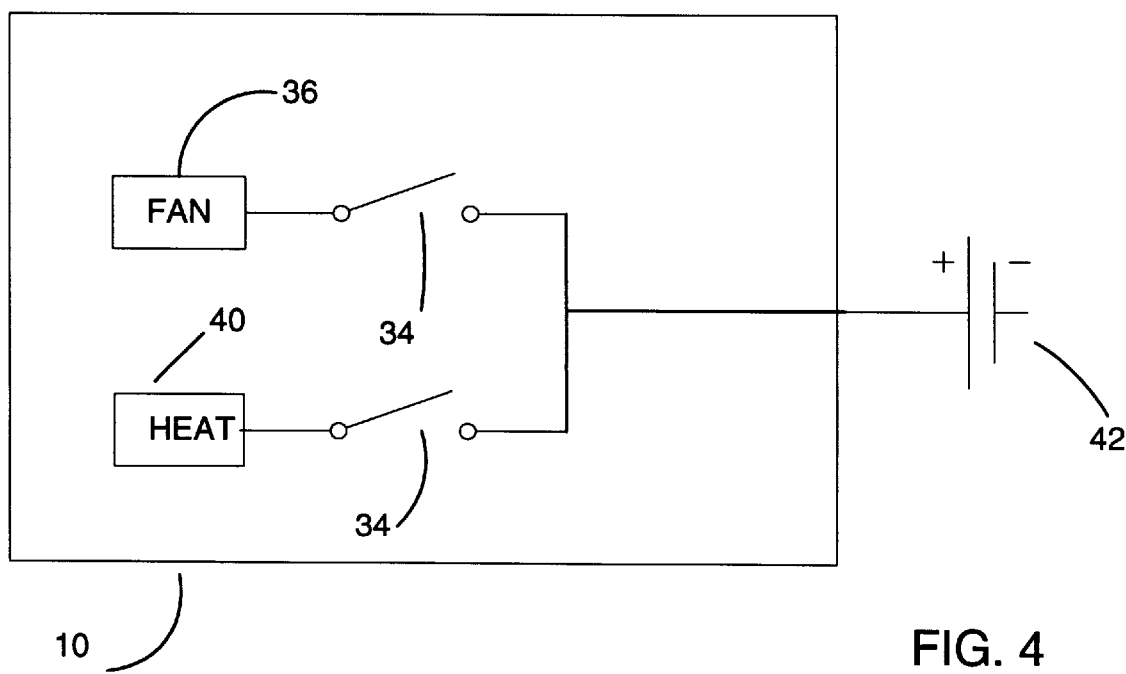
FIG. 4 is a schematic diagram showing generally the relationship between the cooling and heating elements and the external power source.

Ideally the thermostat 34 should be positioned within the case such that it is capable of accurately assessing the average air temperature within the case 10. As shown in FIG. 4, the fan 36 and the silicon strips 40 may be activated by two separate temperature sensitive switches 34. It will be appreciated by one of skill in the art that the fan 36 and silicon strips 40 may be activated by other means such as solid state switching or a thermistor.

As shown in FIG. 4, the thermostat 34 and signal switch 38 are connected to an external power source 42. Where the case 10 is mounted within a vehicle, the external power source 40 would likely be the vehicle battery where the case is mounted on a wall or in an unheated area, the power source would likely be from a standard wall outlet. For cases 10 that are used in a vehicle, a battery protection switch may also be provided to turn heaters and fans off if the voltage of the vehicle battery decreases below a given level. Ideally the vehicle battery voltage should be sufficient to allow the engine to be started. A sufficient battery voltage for a standard 12 volt car battery would be, for example, 9 volts, more preferably 12 volts.

The case 10 may also be provided with flanges 44, or other means, for mounting. For example, it is contemplated that the case could be mounted within the uninsulated trunk of a police, or other emergency, vehicle. Additionally, the case 10 could be mounted on the wall of a building and is particularly suitable for use in a warehouse, or other uninsulated building.

Modifications falling within the scope of the invention will be apparent to those skilled in the art. For example, an evaporative cooler or a compressor based air conditioner may be used as a cooler in addition to, or in place of, the fan above. Also, the case may use the heating and/or cooling system of the vehicle or structure within which the case is mounted or stored. All references cited herein are incorporated by reference in their entirety.

What is claimed:

1. A method of using an environmental chamber, comprising:

placing an electrotherapy device into the environmental chamber;

monitoring a temperature of said electrotherapy device; and maintaining an interior of the environmental chamber within a predetermined temperature range, based on said monitoring, by using a cooler or a heater.

2. The method of claim 1, wherein said predetermined temperature range is from 25° C. to 50° C.

3. The method of claim 1, wherein said maintaining includes circulating air in the environmental chamber.

4. The method of claim 1, wherein said monitoring includes using a thermostat.

5. The method of claim 1, wherein said monitoring includes using a temperature sensitive switch.

6. The method of claim 1, wherein said maintaining includes using a cooler when said temperature reaches a threshold temperature.

7. The method of claim 6, wherein said threshold temperature is between 25° C. and 50° C.

8. The method of claim 6, wherein said cooler is a fan.

9. The method of claim 1, wherein said maintaining includes using a heater when said temperature reaches a threshold temperature.

10. The method of claim 7, wherein said threshold temperature is between −10° C. and 20° C.

11. The method of claim 7, wherein said heater is a heat strip.

* * * * *